United States Patent
Papish et al.

(10) Patent No.: US 9,527,066 B2
(45) Date of Patent: Dec. 27, 2016

(54) DIHYDROXYBIPYRIDINE COMPLEXES OF RUTHENIUM AND IRIDIUM FOR WATER OXIDATION AND HYDROGENATION

(75) Inventors: Elizabeth T. Papish, Philadelphia, PA (US); Ismael Nieto, Exton, PA (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 0 days.

(21) Appl. No.: 14/342,077

(22) PCT Filed: Aug. 27, 2012

(86) PCT No.: PCT/US2012/052518
§ 371 (c)(1),
(2), (4) Date: Feb. 28, 2014

(87) PCT Pub. No.: WO2013/033018
PCT Pub. Date: Mar. 7, 2013

(65) Prior Publication Data
US 2014/0219911 A1 Aug. 7, 2014

Related U.S. Application Data

(60) Provisional application No. 61/528,787, filed on Aug. 30, 2011.

(51) Int. Cl.
| | |
|---|---|
| B01J 31/12 | (2006.01) |
| C01B 3/06 | (2006.01) |
| C25B 1/04 | (2006.01) |
| C01B 13/02 | (2006.01) |
| C07F 15/00 | (2006.01) |
| C01B 3/04 | (2006.01) |
| B01J 31/18 | (2006.01) |

(52) U.S. Cl.
CPC ............ B01J 31/122 (2013.01); B01J 31/181 (2013.01); B01J 31/1815 (2013.01); C01B 3/042 (2013.01); C01B 3/06 (2013.01); C01B 13/0207 (2013.01); C01B 13/0237 (2013.01); C07F 15/0033 (2013.01); C25B 1/04 (2013.01); B01J 2231/70 (2013.01); B01J 2531/821 (2013.01); B01J 2531/827 (2013.01); Y02E 60/364 (2013.01)

(58) Field of Classification Search
None
See application file for complete search history.

(56) References Cited

U.S. PATENT DOCUMENTS

2010/0016618 A1 1/2010 Carreira
2010/0298562 A1 11/2010 Dubreuil et al.

OTHER PUBLICATIONS

Conifer et al. Dalton Trans., 2011, 40, 1031-1033.*
Albrecht, et al., Chelated Iridium(III) Bis-carbene Complexes as Air-Stable Catalysts for Transfer Hydrogenation, Organometallics, 21:3596-3604, 2002.
Blakemore, et al., Half-Sandwich Iridium Complexes for Homogeneous Water-Oxidation Catalysis, J Am Chem Soc, 132:16017-16029, 2010.
Clapham, et al., Mechanisms of the H2-hydrogenation and transfer hydrogenation of polar bonds catalyzed by ruthenium hydride complexes, Coordination Chemistry Reviews, 248:2201-2237, 2004.
Lewis, et al., Correction of Carvedilol sidesteps G proteins, PNAS, 104:20142, 2007.
Depasquale, et al., Iridium Dihydroxybipyridine Complexes Show That Ligand Deprotonation Dramatically Speeds Rates of Catalytic Water Oxidation, Inorg. Chem. 52:9175-9183, 2013.
Gandolfi, et al., Chelating NHC Ruthenium(II) Complexes as Robust Homogeneous Hydrogenation Catalysts, Organometallics, 28:5112-5121, 2009.
Garner, et al., Mononuclear Nitrogen/Sulfur-Ligated Zinc Methoxide and Hydroxide Complexes: Investigating Ligand Effects on the Hydrolytic Stability of Zinc Alkoxide Species, J. Am. Chem. Soc., 124:9970-9971, 2002.
Gärtner, et al., Synthesis, Characterisation and Application of Iridium(III) Photosensitisers for Catalytic Water Reduction, Chem. Eur. J., 17:6998-7006, 2011.
Goldsmith, et al., Discovery and High-Throughput Screening of Hetroleptic Iridium Complexes for Photoinduced Hydrogen Production, J. Am. Chem. Soc., 127:7502-7510, 2005.
Himeda, Conversion of CO2 into Formate by Homogeneously Catalyzed Hydrogenation in Water: Tuning Catalytic Activity and Water Solubility through the Acid—Base Equilibrium of the Ligand, Eur. J. Inorg. Chem., 3927-3941, 2007.
Himeda, et al., Simultaneous Tuning of Activity and Water Solubility of Complex Catalysts by Acid-Base Equilibrium of Ligands for Conversion of Carbon Dioxide, Organometallics, 26:702-712, 2007.
Hull, et al. Reversible hydrogen storage using CO2 and a proton-switchable iridium catalyst in aqueous media under mild temperature and pressures, Nature Chemistry, 4:383-388, 2012.
Hull, et al., Highly Active and Robust Cp* Iridium Complexes for Catalytic Water Oxidation, J. Am. Chem. Soc., 131:25:8730-8731, 2009.
Kawahara, et al., Dehydrogenative Oxidation of Alcohols in Aqueous Media Using Water-Soluble and Reusable Cp*Ir Catalysts Bearing a Functional Bipyridine Ligand, J. Am. Chem. Soc., 134(8):3643-3646, 2012.
Kovacs, et al., Catalytic Hydrolysis of Esters of 2-Hydroxypyridine Derivatives for Cu2+Detection, Inorganic Chemistry, 47:6:1880-1882, 2008.
Lewis, et al., Powering the planet: Chemical challenges in solar energy utilization, PNAS, 103:15729-15735, 2007.

(Continued)

Primary Examiner — Yun Qian
(74) Attorney, Agent, or Firm — Meunier Carlin & Curfman LLC

(57) ABSTRACT

The present invention discloses a class of organometallic catalysts for both hydrogenation and water oxidation. The synthesis and the use of these catalysts for hydrogenation, hydrogen production and water oxidation reactions is also disclosed.

12 Claims, 7 Drawing Sheets

(56) References Cited

OTHER PUBLICATIONS

Lucas, et al., A Modular Approach toward Regulating the Secondary Coordination Sphere of Metal Ions: Differential Dioxygen Activation Assisted by Intramolecular Hydrogen Bongs, J. Am. Chem. Soc., 128:15476-15489, 2006.

McDaniel, Cyclometalated Indium(III) Aquo Complexes: Efficient and Tunable Catalysts for the Homogeneous Oxidation of Water, J. Am. Chem. Soc., 130:210-217, 2008.

MacBeth, et al., O2 Activation by Nonheme Iron Complexes: A Monomeric Fe(III)-Oxo Complex Derived From O2, Science, 289, 938-941, 2000.

Marelius, et al., How Do Proximal Hydroxy or Methoxy Groups on the Bidentate Ligand Affect [(2,2';6',2"-Terpyridine)Ru-(N,N)X] Water-Oxidation Catalysts? Synthesis, Characterization, and Reactivity at Acidic and Near-Neutral pH, Eur. J. Inorg. Chem., 676-689, 2014.

Mareque-Rivas, et al., Quantifying the relative contribution of hydrogen bonding and hydrophobic environments, and coordinating groups, in the zinc(II)-water acidity by synthetic modelling chemistry, Dalton Trans., 1648-1655, 2004.

Natale, et al. The combination of transition metal ions and hydrogen-bonding interactions, Chem Commun., 425-437, 2008.

Nieto, et al., Transfer Hydrogenation in Water via a Ruthenium Catalyst with OH Groups near the Metal Center on a bipy Scaffold, Organometallics, 30:6339-6342, 2011.

Ozawa, et al., A Photo-Hydrogen-Evolving Molecular Device Driving Visible-Light-Induced EDTAReduction of Water into Molecular Hydrogen, J. Am. Chem. Soc., 128:4926-4927, 2006.

Travnicek, et al., Square-planar nickel(II) O,O¢-dialkyldithiophosphato complexes with triphenylphosphine of the type [NiX(S2P{OR}2)(PPh3)] (X ¼ Cl, Br, I and NCS), Transition Metal Chemistry, 29:352-357, 2004.

Umemoto, et al., Synthesis, Properties, and Reactivity of N,N¢-Difluorobipyridinium and Related Salts and Their Applications as Reactive and Easy-To-Handle Electrophilic Fluorinating Agents with High Effective Fluorine Content1, J. Org. Chem., 63:3379-3385, 1998.

Wada, et al., Structural and Spectroscopic Characterization of a Mononuclear Hydroperoxo—Coope (II) Complex with Tripodal Pyridylamine Ligands, Angew. Chem. Int. Ed, 37:798-799, 1998.

Wang, et al., Mechanistic Insight through Factors Controlling Effective Hydrogenation of CO2 Catalyzed by Bioinspired Proton-Responsive Iridium (III) Complexes, ACS Catalysis, 3:856-860, 2013.

Wang, et al., Second-coordination-sphere and electronic effects enhance iridium (III)-catalyzed homogeneous hydrogenation of carbon dioxide in water near ambient temperature and pressure, Energy Environ. Sci., 5:7923-7926, 2012.

Wilson, Hydrogen Oxidation and Production Using Nickel-Based Molecular Catalysts with Positioned Proton Relays, J. Am. Chem. Soc., 128:358-366, 2006.

Wu, et al., Asymmetric Transfer Hydrogenation in Water with Platinum Group Metal Catalysts, Journal Archive, 54:3-19, 2010.

Wu, et al., A novel GC-MS method for rapid determination of headspace oxygen in vials of pharmaceutical formulations, J. Pharm. Bio. Anal., 48:8-12, 2008.

Yamaguchi, et al., Thermal Stability an Absorption Spectroscopic Behavior of (µ-Peroxo)dicopper Complexes Regulated with Intramolecular Hydrogen Bonding Interactions, Eur. J. Inorg. Chem. 4378-4386, 2003.

Zhang, et al., A Biomimetic Copper Water Oxidation Catalyst with Low Overpotential, J. Am. Chem. Soc., 136 (1):273-281, e-pub. Dec. 10, 2013.

Zhang, et al., Copper-mediated dihydroxylation of 2,20-bipyridine-like ligands under solvothermal conditions, Inorganica Chimica Acta, 359:3666-3670, 2006.

International Search Report and Written Opinion for PCT/US2012/052518 dated Jan. 31, 2013.

* cited by examiner

Figure 5. Note that the arrows (┅┅➤) indicate how the spectra change with increasing pH. The curved lines (⌒) show which plots are which final pH values.

Figure 6. Note that the arrows (⇢) indicate how the spectra change with increasing pH. The curved lines (⌒) show which plots are which final pH values.

DIHYDROXYBIPYRIDINE COMPLEXES OF RUTHENIUM AND IRIDIUM FOR WATER OXIDATION AND HYDROGENATION

GOVERNMENT SUPPORT

This invention was made with government support under Contract No. 0846383 awarded by the National Science Foundation. The government has certain rights in the invention.

BACKGROUND OF THE INVENTION

1. Field of the Invention

The present invention relates to the production and use of organometallic catalysts. In particular, it is directed to bipyridyl metal complexes, to processes for preparing these catalysts and uses thereof.

2. Description of the Related Technology

Hydrogenation of $CO_2$ to form methanol is a novel approach toward storage of a hydrogen source. With hydrogen obtained in a carbon neutral fashion, ideally from photolytic water splitting rather than from fossil fuels, $CO_2$ hydrogenation represents a carbon neutral means of hydrogen storage, because $CO_2$ is absorbed during methanol formation and released during the subsequent methanol combustion.

Catalysts for hydrogenation of $CO_2$ are critical for the success of such a strategy, as the conversion rate and turnover frequency for $CO_2$ hydrogenation is very low without effective catalysts. Hydrogenation catalysts are used in many chemical reactions in addition to $CO_2$ hydrogenation. They generally comprise elements of group VIII of the Periodic Table, e.g. iron, cobalt, nickel, ruthenium, rhodium, palladium, platinum and iridium, as active components. Promoters such as copper, silver, gold, zinc, tin, bismuth or antimony may additionally be present.

In addition, catalysts for oxidation of water to molecular oxygen and hydrogen from photolytic water splitting may play an important role in our nation's long-term sustainable-energy policy. The solar energy may be used as the driving force for oxidation of water to produce oxygen and hydrogen, which may be stored and used as pollution free, alternative energy source.

Homogenous catalysts for both of these processes, hydrogenation and water oxidation, are highly desirable. Homogeneous catalysts tend to have higher efficiencies than heterogeneous catalysts, and they allow for mechanistic studies that can lead to an understanding of intimate mechanistic details. Based on such mechanistic studies, the effectiveness of the catalysts may be further improved.

A catalyst is known that is a half-sandwich ruthenium or iridium complex with 4,4'-dihydroxy-2,2'-bipyridine having the formula $[(C_nMe_n)M(H_2L^1)Cl)]Cl$, wherein $H_2L^1$ is 4,4'-dihydroxy-2,2'-bipyridine, M is ruthenium when n=6 and M is iridium when n=5 (Himeda, *Eur. J. Inorg. Chem.*, 3927-3941, (2007)). This catalyst has high catalytic activity and is reusable without substantial waste generation because of the automatic tuning of the catalytic activity and water solubility of the catalyst through the acid base equilibrium of the catalyst ligand. Another example of such a homogeneous catalyst is a bipyridyl complex with iridium having the formula $[Cp*Ir(bpy)H_2O](SO_4)$, where bpy is 2,2'-bipyridine and Cp is a pentamethyl cyclopentadienyl group (US 2010/0016618).

Significant problems still remain in the field of catalytic hydrogenation and water oxidation chemistry. Industrial water splitting as a means of energy storage has yet to be realized, and is potentially a carbon neutral source of hydrogen gas. Hydrogen gas can be a more useful fuel if chemically transformed into other less flammable and more-dense chemicals, and hydrogenation technology provides a means of using hydrogen to create energy dense fuels (for transportation, etc.). However, hydrogenation reactions still often require significant energy input in terms of high pressures and temperatures. Having the ability to catalyze such reactions in aqueous solvents together with high reaction efficiencies would be useful and would save energy.

SUMMARY OF THE INVENTION

In one aspect, the present invention is directed to catalysts useful for either or both of hydrogenation and water oxidation. These catalysts are represented by the formula (I):

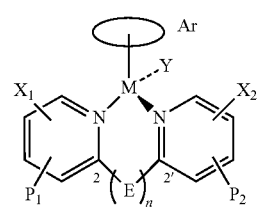

Formula (I)

wherein Ar is a substituted or unsubstituted aromatic ring, M is ruthenium or iridium, $X_1$ and $X_2$ are independently hydrogen bonding groups located at the 4, 5 or 6 position on the pyridine ring, Y is an anionic group, $P_1$ and $P_2$ are located at 4, 5 or 6 position on the pyridine ring and are independently selected from the group consisting of H, alkyl groups, fluorinated alkyl groups, phosphate and sulfonate, the link between pyridine rings (E) may be nothing when n=0 (i.e. they are linked directly without any atoms between the pyridine rings) or when n=1 this group could be C=O, O, $CH_2$, or $CHSO_3$ to provide a sulfonate group, with the proviso that when M is ruthenium, $P_1$ and $P_2$ are H; the pyridine rings are linked directly via a C2 to C2' bond (as in bipyridine) and $X_1$ and $X_2$ are both located at the 6 position, $Ar:X_1:X_2:Y$ are not cymene:OH:OH:Cl; cymene:OMe: OMe:Cl; or $C_6Me_6$:OH:OH:Cl, and when M is iridium, $P_1$ and $P_2$ are H; and there is no link between the pyridine rings, $Ar:X_1:X_2:Y$ is not pentamethylcyclopentadienyl:OH:OH: Cl.

Another aspect of the present invention is directed to methods of synthesizing the catalysts of the formula (I) starting from a compound represented by formula (II):

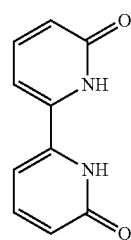

Formula (II)

said method comprising the step of reacting said 6,6'-dihyroxybipyridine with a metal complex. It has been found that a sufficient amount of the compound of the formula (II)

tautomerizes to produce 6,6'-dihydroxybipyridine to react with the metal complex in order to form the catalysts of the present invention.

A further aspect of the present invention is directed to methods of using the catalysts of the formula (I) wherein Ar is a substituted or unsubstituted aromatic ring, M is ruthenium or iridium, $X_1$ and $X_2$ are independently hydrogen bonding groups located at the 4, 5 or 6 position on the pyridine ring, Y is an anionic group, $P_1$ and $P_2$ are located at 4, 5 or 6 position on the pyridine ring and are independently selected from the group consisting of H, alkyl groups, phosphate and sulfonate, the link between pyridine rings (E) may be nothing when n=0 (i.e. they are linked directly without any atoms between the pyridine rings) or when n=1 this group could be C=O, O, $CH_2$, or $CHSO_3$ to provide a sulfonate group, for hydrogenation, water oxidation and hydrogen generation.

DETAILED DESCRIPTION OF THE PREFERRED EMBODIMENT(S)

Figure 1:
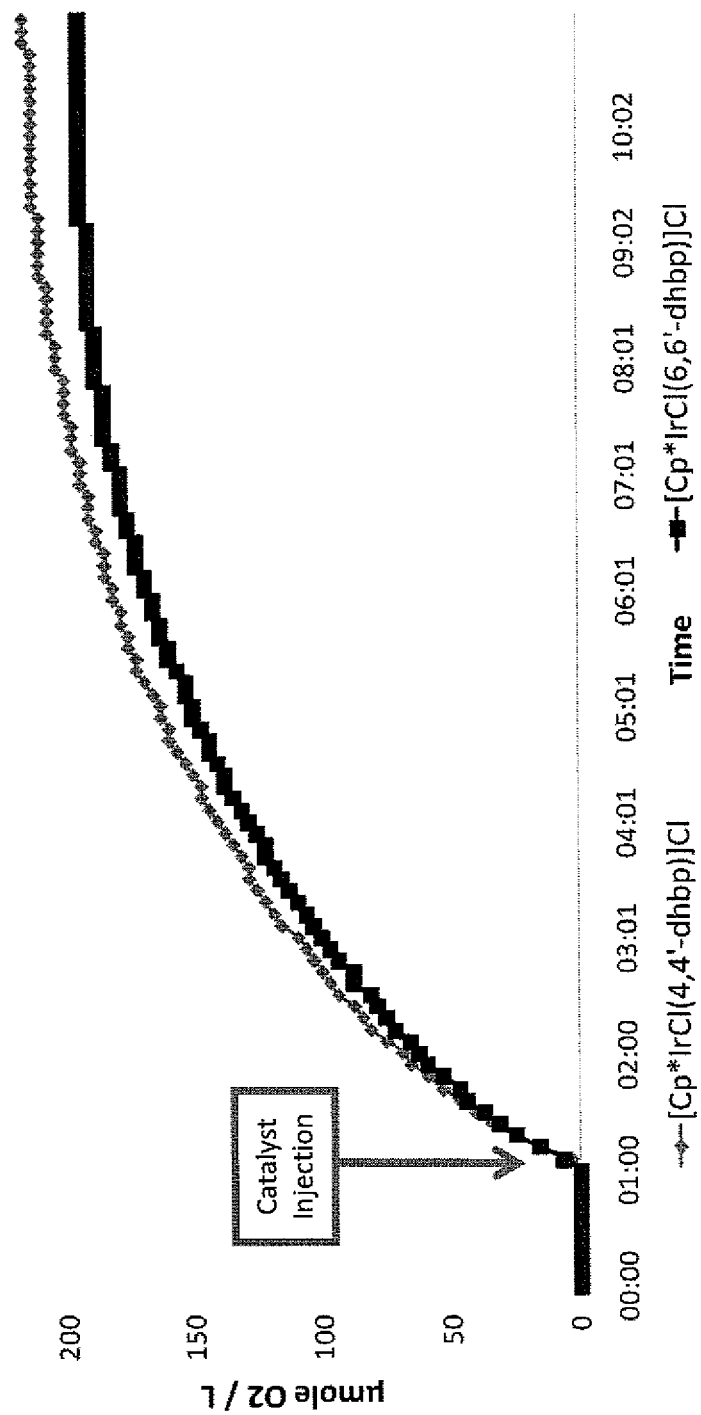
FIG. 1 shows the rate of generation of $O_2$ from water oxidation over time with two different catalysts.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In a first aspect, the present invention relates to organometallic catalysts useful for both hydrogenation and water oxidation. These catalysts can be represented by the formula (I):

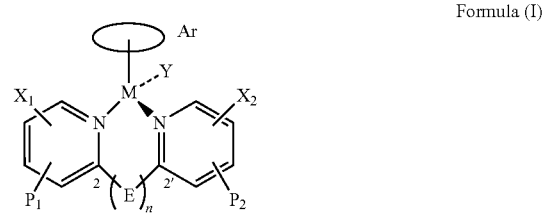

Formula (I)

wherein Ar is a substituted or unsubstituted aromatic ring, M is ruthenium or iridium, $X_1$ and $X_2$ are independently hydrogen bonding groups located at the 4, 5 or 6 position on the pyridine ring, Y is an anionic group, $P_1$ and $P_2$ are located at 4, 5 or 6 position on the pyridine ring and are independently selected from the group consisting of H, alkyl groups, fluorinated alkyl groups, phosphate and sulfonate, the link between pyridine rings (E) may be nothing when n=0 (i.e. they are linked directly without any atoms between the pyridine rings) or when n=1 this group may be C=O, O, $CH_2$, or $CHSO_3$ to provide a sulfonate group, with the proviso that when M is ruthenium, $P_1$ and $P_2$ are H; the pyridine rings are linked directly via a C2 to C2' bond (as in bipyridine) and $X_1$ and $X_2$ are both location at the 6 position, Ar:$X_1$:$X_2$:Y are not cymene:OH:OH:Cl; cymene:OMe:OMe:Cl; or $C_6Me_6$:OH:OH:Cl, and when M is iridium, $P_1$ and $P_2$ are H; there is no link between the pyridine rings Ar:$X_1$:$X_2$:Y is not pentamethylcyclopentadienyl:OH:OH:Cl.

The aromatic group Ar is preferably selected from aromatic groups containing five and six membered rings. Exemplary aromatic groups with six membered rings include, but are not limited to, benzene or benzene substituted by one or more substituents each independently selected from the group consisting of alkyl, alkenyl, alkynyl, fluoroalkyl and haloalkenyl, phenyl, ammonium, carboxylic acid, acetyl, and combinations thereof, preferably having up to 36, more preferably, up to 24, and most preferably up to 12 carbon atoms. Examples of suitable aromatic groups include, but are not limited to, benzene, cymene, tetramethylbenzene, hexamethylbenzene, t-butylbenzene, 1,3-diethylbenzene, 1,4-diethylbenzene, toluene and xylene.

Exemplary aromatic groups with five membered rings include cyclopentadienyl, substituted cyclopentadienyl, indenyl or substituted indenyl and fluorenyl or substituted fluorenyl. Specific examples of these aromatic groups include, but are not limited to, cyclopentadienyl, methylcyclopentadienyl, dimethylcyclopentadienyl, trimethylcyclopentadienyl, tetramethylcyclopentadienyl, pentamethylcyclopentadienyl, ethylcyclopentadienyl, n-propylcyclopentadienyl, isopropylcyclopentadienyl, n-butylcyclopentadienyl, sec-butylcyclopentadienyl, tert-butylcyclopentadienyl, n-pentylcyclopentadienyl, neopentylcyclopentadienyl, n-hexylcyclopentadienyl, n-octylcyclopentadienyl, phenylcyclopentadienyl, naphthylcyclopentadienyl, trimethylsilylcyclopentadienyl, triethylsilylcyclopentadienyl, tert-butyldimethylsilylcyclopentadienyl, indenyl, methylindenyl, dimethylindenyl, ethylindenyl, n-propylindenyl, isopropylindenyl, n-butylindenyl, sec-butylindenyl, tert-butylindenyl, n-pentylindenyl, neopentylindenyl, if n-hexylindenyl, n-octylindenyl, n-decylindenyl, phenylindenyl, methylphenylindenyl, naphthylindenyl, trimethylsilylindenyl, triethylsilylindenyl, tert-butyldimethylsilylindenyl, tetrahydroindenyl, fluorenyl, methylfluorenyl, dimethylfluorenyl, ethylfluorenyl, diethylfluorenyl, n-propylfluorenyl, di-n-propylfluorenyl, isopropylfluorenyl, diisoproylfluorenyl, n-butylfluorenyl, sec-butylfluorenyl, tert-butylfluorenyl, di-n-butylfluorenyl, di-sec-butylfluorenyl, di-tert-butylfluorenyl, n-pentylfluorenyl, neopentylfluorenyl, n-hexylfluorenyl, n-octylfluorenyl, n-decylfluorenyl, n-dodecylfluorenyl, phenylfluorenyl, diphenylfluorenyl, methylphenylfluorenyl, naphthylfluorenyl, trimethylsilylfluorenyl, bis-trimethylsilylfluorenyl, triethylsilylfluorenyl, and tert-butyldimethylsilylfluorenyl.

The hydrogen bonding groups $X_1$ and $X_2$, which provide protons for the hydrogenation and water oxidation reactions, are preferably located close to the metal center of the catalysts. $X_1$ and $X_2$ may be independently located at the 4, 5 or 6 position of the pyridine ring, but more preferably are located at the 6 position of the pyridine ring where they are closer to the metal center. Placing the hydrogen bonding groups $X_1$ and $X_2$ close to the metal center can modulate the proton transfer, therefore making the hydrogenation and water oxidation reactions more efficient.

$X_1$ and $X_2$ may be the same or different, and each is independently selected from the group consisting of hydroxyl, alcohol, carboxylic acid, amides containing an —NH group and amines.

The anionic group Y may be linked to the metal center and may act as a leaving group for the hydrogenation and water oxidation reactions. Examples of the anionic group include, but are not limited to, halogens such as $F^-$, $Cl^-$, $Br^-$ and $I^-$, alkoxy groups, $PF_6^-$, $BF_4^-$, $B(ArF)_4^-$, $ClO_4^-$, $SbF_6^-$, $SO_4^{2-}$, trifluoroacetate, and thiocyanates. When Y is $PF_6^-$, $BF_4^-$, $B(ArF)_4^-$, $ClO_4^-$, $SbF_6^-$, $SO_4^{2-}$, and trifluoroacetate, the anionic group Y is not typically linked to the metal center, and in some cases water or other solvent molecules may be bound to the metal center.

The link between pyridine rings (E) may be nothing when n=0 (i.e. they are linked directly without any atoms between the pyridine rings) or when n=1 this group could be C=O, O, $CH_2$, or $CHSO_3$ to provide a sulfonate group. While the above examples are preferable, the link could also contain one B, N, P or Si atom and/or consist of one-two carbon atoms.

$P_1$ and $P_2$ are located at the 4, 5 or 6 position on the pyridine ring. $P_1$ and $P_2$ are independently selected from the group consisting of H, alkyl groups, fluorinated alkyl groups, phosphate and sulfonate. $P_1$ and $P_2$ may be used to tune the solubility of the catalysts of the present invention. In one embodiment, inclusion of a phosphate group as $P_1$ and/or $P_2$ will make the catalyst more water-soluble. $P_1$ and $P_2$ may also be used for attachment of the catalyst to a solid support or for allowing the catalyst to bind $Ca^{2+}$.

The present application uses the Formula I as shorthand representation of the catalysts of the present invention only. The present invention envisions that any selection of any functional group can be combined with any selection of every other functional group in Formula I. These functional groups include M, Ar, $X_1$, $X_2$, Y, $P_1$, $P_2$ and the linker E. To illustrate by examples, M is selected from ruthenium or iridium. Each one of the three selections for M may be combined with every selection for Y, which may include halogens such as F, Cl, Br and I, alkoxy groups, $PF_6^-$, $BF_4^-$, $B(ArF)_4^-$, $ClO_4^-$, $SbF_6^-$, $SO_4^{2-}$, and trifluoroacetate, and thiocyanates. Furthermore, each of the numerous embodiments of the catalyst based on the combinations of the selections of every functional group on Formula I may be used with any of the hydrogenation solvents, or hydrogenation agents, or oxidation agents described in the present application.

The catalyst of the present invention is easily tunable by adding, removing or altering external stimuli, such as changing pH or adding a Lewis acid. The tuning is quick, reversible and dramatic. The catalysts may be tuned or "switched" between active and inactive forms, as well as soluble and insoluble forms. For example, one way of switching between active and inactive forms is by protonating and deprotonating the catalyst as described, for example, in Himeda, *Eur. J. Inorg. Chem.*, 3927-3941, (2007).

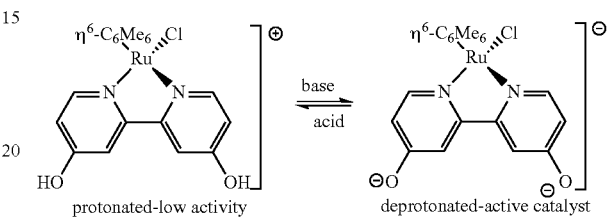

protonated-low activity       deprotonated-active catalyst

Synthesis of the catalysts of the present invention may be carried out using the following process. The synthesis of 6,6'-dihyroxybipyridine (DHBP) may be started from 2-chloro-6-methoxypyridine and be carried out via the three steps set forth below:

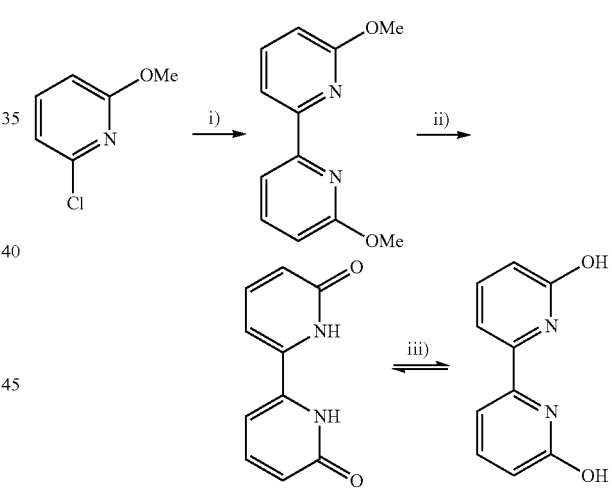

In the first step (i), 2-chloro-6-methoxypyridine is treated with 0.3 eq. $NiCl_2(PPh_3)_2$, Zn(metal), and $^nBu_4NBr$ in dimethylformamide (DMF). The reaction mixture is continuously stirred for 1 day at 55° C. This step produces 6,6'-dimethoxybipyridine.

In the second step (ii), 6,6'-dimethoxybipyridine, the product of step (i), undergoes hydrolysis in 33% HBr in acetic acid. More specifically, the 6,6'-dimethoxybipyridine is dissolved in a solution of HBr at 33% in acetic acid. The reaction mixture is continuously stirred at 120° C. for 2 days. This step produces bipyridinone, a dilactam.

As shown in the scheme above, a certain amount of the bipyridinone tautomerizes to give a DHBP ligand which is the product of step iii). Treatment of the bipyridinone with a metal complex in DMF or methanol, such as 0.5 eq. of [(p-cymene)$RuCl_2$]$_2$ in DMF under inert conditions at 60° C. for 1 day produces the complex of the formula (III):

Formula (III)

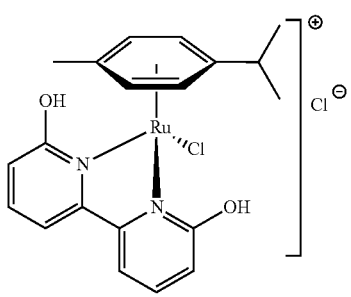

The x-ray crystal structure of the complex of the formula (III) clearly shows that the product has a dihydroxybipyridine ligand.

For the category of catalysts with hemilabile group Ar being cyclopentadienyl or its derivatives, one exemplary final step for synthesis the catalyst is by treatment of the bipyridinone with 0.5 eq. of [(pentamethylcyclopentadienyl)IrCl₂]₂ in dimethylformamide or methanol under inert conditions at 60° C. for 1 day. This reaction produces a catalyst according to present invention, represented by the formula (IV):

Formula (IV)

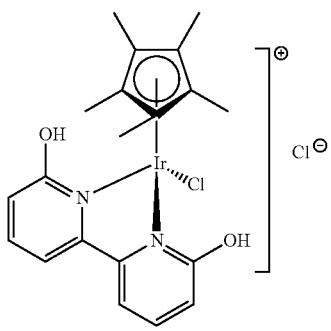

The catalyst of the present invention may be further modified to provide alternative catalysts of the formula (V) and (VI) below:

Formula (V)

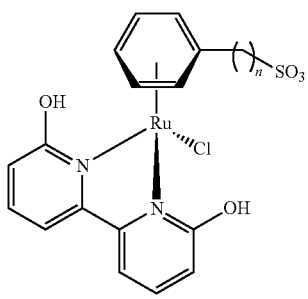

Formula (VI)

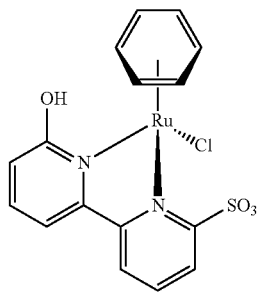

In the above structures, sulfonate is covalently attached to the ligand, as a site for binding group II metal ions, e.g. Ca(II) and Mg(II), as well as Li(I). The length of the chain connecting the sulfonate to the ligand is variable, and n is preferably 0-3, but is not limited to those values. The linking group between the arene ring and the sulfonate is not limited to alkyl, and could contain, for example, aromatic groups, an alkyne group, or other groups. The sulfonate could also be attached to the pyridine ring. Similar complexes can be made with Ir as shown in the formula (VII) and (VIII) below:

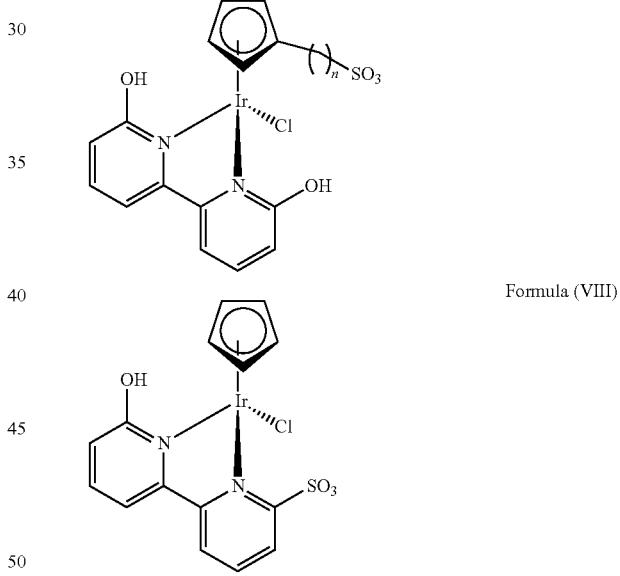

The geometry is important in order to favor binding an additional metal other than the Ru or Ir, as shown below:

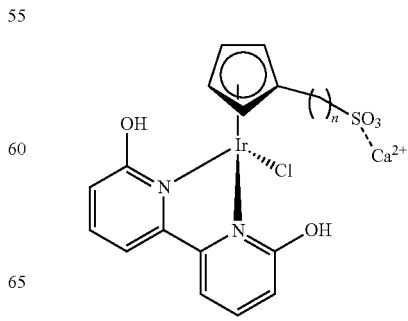

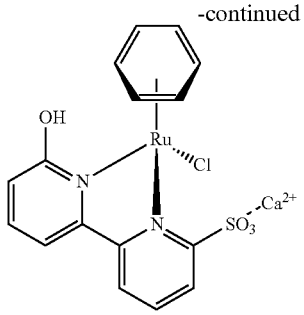

The geometry should be such as prevent binding to Ru or Ir in general and favor binding to a group II metal or Li(II). The placement of the sulfonate is also important in terms of being far enough away from the metal binding group of the ligand so that the ligand's electronic properties are not perturbed. Thus, the sulfonate is far enough away to not perturb the electronics of the ligand, but not so far away in that it can easily reach the Ru/Ir and bind to that instead of Ca.

The use of calcium binding sites is of interest because nature's means of oxidizing water uses a calcium ion in the active site, in close proximity to Mn ions (See Umena, Y., Kawakami, K., Shen, J.-R., & Kamiya, N. (2011). Crystal structure of oxygen-evolving photosystem II at a resolution of 1.9 Å. *Nature*, 473 (7345), 55-60). In this method, Ru or Ir plays a similar role to Mn, and a calcium ion may similarly accelerate the water oxidation.

The catalysts of the present invention feature nitrogen donor groups in a bidentate arrangement. In the case that the catalysts are used for hydrogenation, the hydrogen bonding groups $X_1$ and $X_2$ are placed in close proximity to the metal center to allow for cooperative transfer of hydride from the metal center and $H^+$ from the nearby hydrogen bonding groups $X_1$ and $X_2$ to an appropriate substrate (e.g. ketone or $CO_2$). Furthermore, in the case that the catalysts are used for hydrogenation or water oxidation, the charge on the catalysts may be varied through means such as using cyclopentadienyl or arene as Ar; and using protonated, deprotonated, or neutral hydrogen bonding groups $X_1$ and $X_2$ for a localized +1, 0, or −1 charge, respectively. The likely overall charge on the complex may be +2, +1, 0 or −1. In the case that the catalysts are used for hydrogenation, this can greatly change the acidity of hydride or dihydrogen ligands and for both types of catalysis enhance the solubility and the electron donor properties of the catalysts of the present invention. These desirable features may be achieved via the selection of substrates used in the final step (iii) of the synthesis process charge and solubility can be varied to the desired level. Furthermore, the Y groups can be exchanged with each other by salt metathesis after the complex is synthesized.

The hydrogen bonding groups $X_1$ and $X_2$ may be useful in catalyst recycling since it is possible to react the catalyst with a bead, such as a silica bead, using the hydrogen bonding groups in order to attach the catalyst to the beads. Also, the $P_1$ and $P_2$ groups, especially sulfonate and phosphate groups, may also be used for this type of catalyst recycling. Once attached to the beads, the catalyst can easily be separated from the reaction mixture.

The catalysts of the present invention are metal-ligand multifunctional complexes. Within the scope of the invention, the properties of the complexes may be varied by hydrogen bonding, modification of the charge and modification of the electronics. The catalysts of the present invention may be used for various hydrogenation reactions. The catalysts may be water-soluble and therefore provide an important advantage of enabling the hydrogenation to be carried out in an aqueous environment such as an aqueous solution.

One exemplary application of the catalysts of the present invention is for the hydrogenation of $CO_2$, which can be used to reduce the greenhouse gas in the atmosphere. $CO_2$ may be converted to formic acid or methanol by this hydrogenation process. In particular, the catalysts may be able to catalyze $CO_2$ hydrogenation to formic acid with high turnover frequencies and/or turnover numbers. The hydrogenation reaction may be carried out, in one embodiment, in a KOH solution at a pressure of 6 MPa at about 60-120° C. The catalyst may be highly diluted in the reaction solution, for example at about $2 \times 10^{-6}$M to about 0.1 M, more preferably, 0.0001 to about 0.01 M. One example of a suitable process uses a $CO_2/H_2$ ratio of 1:1 at a pressure of 4 MPa and a temperature of 80° C. for a 20 hour reaction period. The complex catalyst may be provided at a concentration of 0.1 mM in a 1 M KOH solution.

The principle of microscopic reversibility says that a process in the forward direction occurs by the same microscopic steps in the reverse direction. The catalysts of the present invention catalyze transfer hydrogenation of ketones with formic acid or formate as the hydrogen source, this generates $CO_2$ as a byproduct. The microscopic reverse of this process is $CO_2$ hydrogenation to form formic acid or formate (if an appropriate base is present). Thus, since our catalysts catalyze the forward process, they should also catalyze reverse process, as long as there is a sufficient driving force for the reverse reaction. This driving force can be provided, for example, by using a high pressure of $CO_2$ and $H_2$ gas, and by using a base that makes the process thermodynamically more favorable.

Another exemplary application for the catalysts of the present invention is for hydrogenation of organic substrates, such as ketones and imines Again, these hydrogenation reactions may be carried out in a suitable solvent, preferably containing water, which is highly desirable from an environmental standpoint. The use of water can allow for elimination of hazardous solvents and can make hydrogenation a green and sustainable process. Suitable hydrogenation solvents include water, alcohols, supercritical $CO_2$, propylene carbonate, trifluoroethanol, acetonitrile, and ionic liquids, as well as any other organic solvent or mixtures of the above solvents.

The hydrogenation reactions also need suitable hydrogenation agents, which provide hydrogen to the substrate. Examples of hydrogenation agents include, but are not limited to, $H_2$, formic acid, isopropanol and combinations thereof. Hydrogenation may be carried out in the presence of a suitable base such as KOH or sodium formate, if desired. Hydrogen gas is a suitable source of hydrogen for the reaction.

Another exemplary application for the catalysts of the present invention is for water oxidation. The hydrogen provided by water oxidation is a clean, renewable energy that can help to reduce petroleum consumption. Water splitting by sunlight is ideally compartmentalized into water oxidation and reduction, because this allows the separation of products that would otherwise react with each other. Compartmentalization also allows the use of two separate catalysts, one for oxidation and one for reduction. Water oxidation involves converting two equivalents of water to four electrons and four protons, and generating $O_2$. The hydrogen bonding groups near the metal center in the catalysts can facilitate this oxidation process. Certain catalysts of the present invention may be useful for sunlight driven water oxidation and may potentially provide high turnover numbers and high turnover frequencies.

Water oxidation may be carried out with a suitable oxidizing agent such as Ce(IV)-containing oxidation agents, as well as mild oxidizing agents known to skilled persons (e.g. periodate is our preferred oxidant). Suitable oxidation agents may contain one or more metals in a high oxidation state, or one or more non-metals in a high oxidation state (e.g. periodate). The oxidizing agent includes, but is not limited to, sodium periodate, $(NH_4)_2Ce(NO_3)_6$, persulfates, cobalt (III) complexes, ruthenium (III) complexes, an electric field (an oxidizing electric potential) and light energy (e.g. sunlight). Water oxidation can be carried out under the conditions set forth in, for example, Hull, Jonathan F., et al., "Highly Active and Robust Cp* Iridium Complexes for Catalytic Water Oxidation," *J. Am. Chem. Soc.*, Vol. 131, No. 25 (2009), pp. 8730-31, and McDaniel, Neal D., "Cyclometalated Iridium(III) Aquo Complexes: Efficient and Tunable Catalysts for the Homogeneous Oxidation of Water," *J. Am. Chem. Soc.*, Vol. 130, No. 1, (2008), pp. 210-217.

Another use of the catalyst of the present invention would be for hydrogen generation, preferably using sunlight as an energy source. In this manner, sunlight can be converted to renewable and storable energy in the form of hydrogen. Hydrogen production from protons and electrons in accordance with the present invention is carried out as follows:

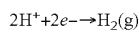
$$2H^+ + 2e^- \rightarrow H_2(g)$$

When combined with water splitting, the basic scheme is this:

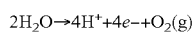
$$2H_2O \rightarrow 4H^+ + 4e^- + O_2(g)$$

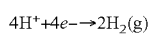
$$4H^+ + 4e^- \rightarrow 2H_2(g)$$

Thus the net reaction is splitting of water to get $O_2$ and $H_2$. Typically these oxidative and reductive reactions require different catalysts and are separated from each other. This is shown in FIG. 1 of Lewis, Nathan S, and Nocera, Daniel G., "Powering the planet: Chemical challenges in solar energy utilization," *PNAS*, Oct. 24, 2007, vol. 103, no. 43, pp. 15729-15735, as corrected in *PNAS*, Dec. 11, 2007, vol. 104, no. 50, p. 20142.

The water oxidation catalyzed by the catalysts of the present invention may be driven, at least partially, by sunlight or electricity. The hydrogen generated by the water oxidation may be stored using the catalyst of the present invention. In some embodiments, hydrogen may be stored by ketone hydrogenation or $CO_2$ hydrogenation, preferably catalyzed by a catalyst of the present invention.

Exemplary conditions for proton reduction to form $H_2$ gas can be found in Wilson, Aaron D., "Hydrogen Oxidation and Production Using Nickel-Based Molecular Catalysts with Positioned Proton Relays," *J. Am. Chem. Soc.*, 2006, vol. 128, pp. 358-366.

Certain catalysts of the present invention have many desirable features, such as a high efficiency, catalyst recycling by self-precipitation, and that they are usable in a substantially waste-free process, are suitable for aqueous reactions, and typically prevent reverse reactions. Further, the catalysts overcome many of the problems occurring in the hydrogenation of $CO_2$ catalyzed by known catalysts. The catalysts can potentially achieve over a 100 or even possibly a 1000-fold increase in catalytic activity relative to some conventional catalysts as a result of the strong electron-donating group on the catalyst ligand.

The catalysts of the present invention may be reused because they can self-precipitate at the end of the $CO_2$ hydrogenation reaction and thus can be easily recycled. Furthermore, the three components (i.e., catalyst, product, and solvent) can be easily separated using conventional filtration and evaporation techniques without significant waste generation, which is highly unusual for processes involving homogenous catalysts. Therefore, the catalysts of the present invention have the combined advantages of both homogeneous (i.e., high catalytic performance) and heterogeneous (i.e., the simplicity of catalyst separation) catalysts.

In one embodiment, $CO_2$ hydrogenation with catalyst recycle may be carried out as follows. A degassed aqueous 0.1 M KOH solution (50 mL) of catalyst (1.5 mg, 2.5 mmol) saturated with $CO_2$ in a 100 mL stainless steel reactor. The reactor was heated at 60° C. and then re-pressurized under 6 MPa of $CO_2:H_2(1:1)$. After stirring for 20 hours, the solution was allowed to stir under a reduced pressure for 2 hours at room temperature and was then cooled to 0° C. in a refrigerator for 12 hours. The suspension was filtered through a 0.2 μm PTFE filter membrane to recover the catalyst precursor.

Embodiments of the catalysts of the present invention are also robust, and stable in air. These features enhance the useful life of the catalysts working longer and facilitate storage of the catalysts for extended periods. The present invention is further illustrated by the following examples. More details on Examples 1-4 may be found in Nieto, I., Livings, M. S., Sacci, J. B. I., Reuther, L. E., Zeller, M., & Papish, E. T. (2011). Transfer Hydrogenation in Water via a Ruthenium Catalyst with OH Groups near the Metal Center on a bipy Scaffold. *Organometallics*, 30(23), 6339-6342, which is incorporated herein in its entirety by reference.

EXAMPLES

Example 1

A 5 ml degassed water solution of 0.10 M $(NH_4)_2Ce(NO_3)_6$ was placed in a 25 ml round bottom flask. The flask was sealed with a rubber septum and purged with nitrogen gas. A stock degassed water solution of 34 μM [Cp*IrCl(DHBP)]Cl was also prepared, placed in a 25 ml round bottom flask, sealed with a rubber septum, and purged with nitrogen. The sealed flasks were transported to a GC/MS instrument (Perkin Elmer Clarus 500 coupled Gas Chromatograph and Mass spectrometer) for headspace GC-MS analysis. The GC/MS instrument used helium as a carrier gas and a Perkin Elmer Elite column (5M5, 30 m×0.25 mm×0.25 μm). The headspace experiment was a 2 minute run based on a literature method described in Wu, L.; Shen, X.-M.; Liu, D. Q. *J. Pharm. Bio. Anal.* 2008, 48, 8-12, with the GC oven initially held at 50° C. for 1 minute and then ramped up to 100° C. in 1 minute. Injection of reaction sample was performed by manual injection on GC/MS instrument. Once the instrument was ready for analysis, headspace samples (25 μl quantity by gastight syringe) were taken of the room air and the flask containing $(NH_4)_2Ce(NO_3)_6$ as control data (both the room air and the sealed flask showed a broad spike at 1.6-1.8 minutes in the chromatogram, with the flask containing a minimal presence of $O_2$ ([mass=32] 0.51% total ion chromatogram (TIC))). After reviewing the control data, 5 ml of 34 μM [Cp*IrCl(DHBP)]Cl stock solution was added to the flask containing $(NH_4)_2Ce(NO_3)_6$ by airtight syringe. The reaction was left to stir 2 hours and after every 20 minutes of the reaction, a head space sample (25 μl quantity by gastight syringe) was taken and analyzed by GC/MS to detect the formation of $O_2$ (Mass=32). Over the course of 60 minutes, there was an increase of 3.3% TIC accounting for $O_2$ formation. In the period of 60-120 minutes, GC/MS data reached a plateau. The results from GC/MS head space analysis are shown in Table 1.

TABLE 1

GC/MS head space experiment for $O_2$ formation [mass = 32]

| Time | % TIC |
|---|---|
| 0 | 0.51 |
| 20 | 2.42 |
| 40 | 3.35 |
| 60 | 3.81 |
| 80 | 3.55 |
| 100 | 3.63 |
| 120 | 3.49 |

Example 2

One exemplary catalyst according to present invention represented by formula:

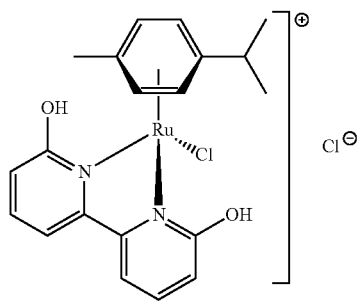

was used for hydrogenation of several different organic substrates. For ketones, the reaction was carried out by mixing 1 mole % of catalyst, 10:90 of MeOH:water and $NaO_2CH$, and heated to reflux for 16-18 hours. For imines, the reaction was carried out by mixing 1 mole % of catalyst, THF, $NEt_3$ base (5 molar %) and 75 psi $H_2(g)$, with heating to reflux for 48 hours. The catalyst provided a very high percentage conversion for ketones in water. The results are shown in Table 2.

TABLE 2

Hydrogenation of Ketones

| Substrate | % conversion | Turnover frequency $(h^{-1})$ | Turnover number |
|---|---|---|---|
| acetophenone | 97 | 16.17 | 97 |
| 2'-acetonaphtone | 81 | 13.50 | 81 |
| 4-bromo-acetophenone | 97 | 16.17 | 97 |
| 4-methoxy-acetophenone | 65 | 10.71 | 65 |
| 2-methoxy-acetophenone | 53 | 8.83 | 53 |
| N-benzylidene-methylamine | 30 | 0.63 | 30 |

Example 3

One exemplary catalyst according to present invention represented by the formula:

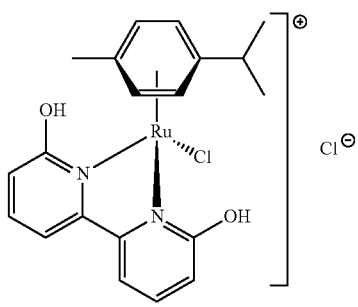

was used to catalyze hydrogenation of acetophenone under various conditions. For each mole of the substrate, 5 moles of a base is used. The reaction is carried out at 90° C. for 16-17 hours. The results are shown in Table 3 below.

TABLE 3

Hydrogenation of Acetophenone

| Mole % catalyst | Base ($H_2$ source) | Solvent | % conversion |
|---|---|---|---|
| 5 | $NaO_2CH/HO_2CH$ | $H_2O$ | 89 |
| 5 | $NaO_2CH$ | $H_2O$ | 89 |
| 1 | $NaO_2CH$ | $H_2O$ | 31 |
| 1 | $NaO_2CH$ | 50/50 MeOH/$H_2O$ | 96 |
| 1 | $NaO_2CH$ | 10/90 MeOH/$H_2O$ | 97 |

Example 4

Five catalysts were used to catalyze hydrogenation of acetophenone. The first four are represented by the following structures:

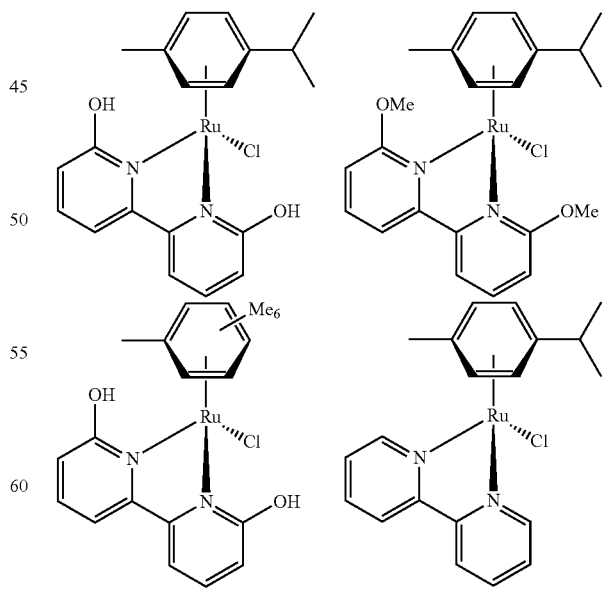

These catalysts are represented as 1-4 in Table 4. The last catalyst is $[(\eta^6\text{-p-cymene})RuCl_2]_2$. The reaction mixture contained 0.02 mmole catalyst, 10 mmole of $NaO_2CH$ or 2 mmole of KOH, 0.667 mmole of 1,3,4-trimethoxybenzene as internal standard, and 10 mL solvent. The reaction was carried out under $N_2$ at 85-90° C. for 24 hours unless otherwise stated (x=18 hours, y=20 hours, z=21 hours). The percentage conversion was determined by $^1H$-NMR as an average of two trials. The results are shown in Table 4 below.

TABLE 4

Hydrogenation of Acetophenone

| Base | Solvent | % Conversion | | | | [p-cymRuCl$_2$]$_2$ |
|---|---|---|---|---|---|---|
| | | 1 | 2 | 3 | 4 | |
| KOH | $^iPrOH$ | 100 | 100$^y$ | 100$^z$ | 98 | 100 |
| $NaO_2CH$ | $H_2O$ | 29$^x$ | 13$^y$ | 15$^z$ | 5 | 13 |
| $NaO_2CH$ | 50/50 MeOH/$H_2O$ | 96$^x$ | 19$^y$ | 39$^z$ | 12 | 13 |
| $NaO_2CH$ | 10/90 MeOH/$H_2O$ | 95$^x$ | 22$^y$ | 50$^z$ | 22 | 15 |

Example 5

A catalyst according to the present invention was used for water oxidation. The catalyst may be represented by Cp*IrCl(n,n'-DHBP)]Cl. More specifically, 5 μM of Cp*IrCl(n,n'-DHBP)]Cl and 78 mM CAN (CeNH$_4$NO$_3$) are added. Two variations of the catalyst were used Cp*IrCl(4,4'-DHBP)]Cl and Cp*IrCl(6,6'-DHBP)]Cl. The vessel and catalyst solution were maintained at 25° C. The results showing generation of $O_2$ over time are shown in FIG. 1. It was also observed that [Cp*IrCl(bipy)]Cl had an initial rate (mole $O_2$ $L^{-1}$ $s^{-1}$) of 72±3 and a turnover frequency (TOF) of 14.4±0.7. Details are given below in Table 5.

TABLE 5

Water Oxidation

| Catalyst | Initial Rate (μmole $O_2$ $L^{-1}$ min$^{-1}$)$^a$ | TOF (min$^{-1}$)$^a$ | TON$^b$ | TOF (min$^{-1}$)$^b$ |
|---|---|---|---|---|
| [Cp*IrCl(6,6'-DHBP)]Cl | 75.00 ± 15 | 15.07 ± 15 | 38.93 | 3.89 |
| [Cp*IrCl(4,4'-DHBP)]Cl | 81.25 ± 12 | 16.33 ± 12 | 43.34 | 4.33 |

$^a$first 30 seconds of reaction;
$^b$first 10 minutes of reaction.
TON is turn over number.

Example 6

Catalysts were used for water oxidation with $NaIO_4$ as an oxidant. 5 μM of iridium catalyst represented below were added to the reaction mixture (labeled as 4,4'-DHBP, 6,6'-DHBP, 4,4'-dmeobp and bipy respectively in Table 6):

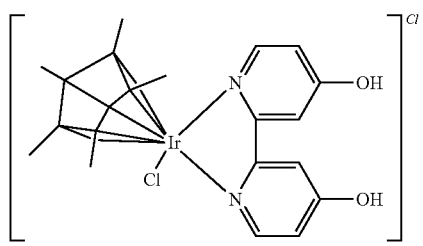

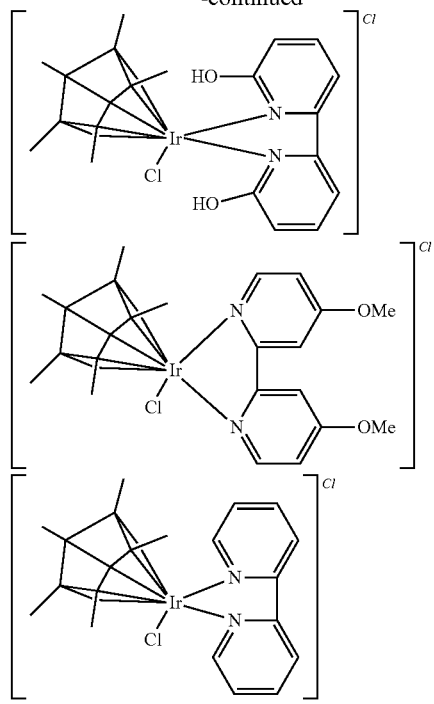

20 mM of $NaIO_4$ was added. The pH was 5.6 and NaOAc was used as a buffer. The vessel and catalyst solution were maintained at 25° C. The results for generation of $O_2$ over time are summarized below:

TABLE 6

Water Oxidation

| Catalyst | Initial Rate: (μM $O_2$ min$^{-1}$) "first 30 sec" | TOF (min$^{-1}$) | 10 min: TON, TOF (min$^{-1}$) |
|---|---|---|---|
| 4,4'-DHBP | 106.25 ± 3 | 21.35 ± 3 | 118.70, 11.87 |
| 6,6'-DHBP | 50 ± 3 | 10.04 ± 3 | 99.86, 9.99 |
| 4,4'-dmeobp | 0 ± 3 | 0 ± 3 | 6.75, 0.67 |
| bipy | 0 ± 3 | 0 ± 3 | 0.64, 0.064 |

Figure 2:
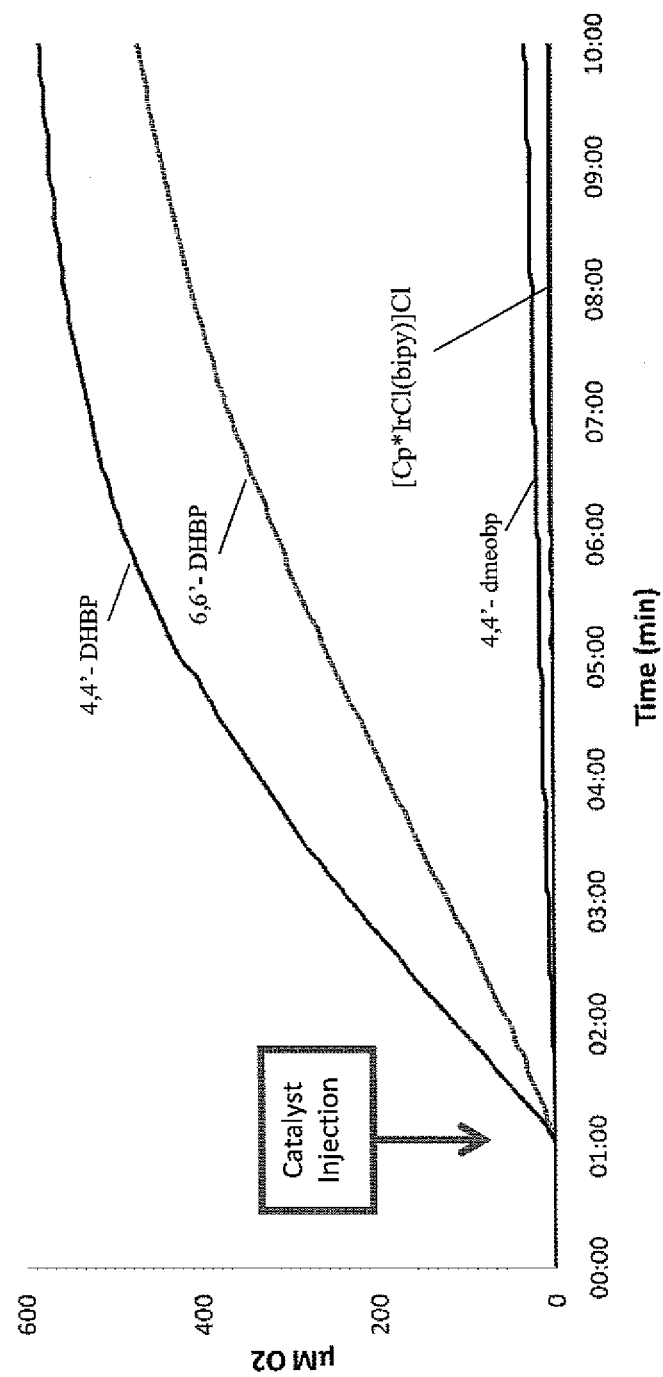
FIG. 2 shows the rate of generation of $O_2$ from water oxidation over time with $NaIO_4$ as oxidant and using four different catalysts [Cp*IrCl(N,N)]Cl, where (N,N) is defined above each set of data.

A plot of the $O_2$ generation over time is also shown in FIG. 2.

Example 7

Figure 3:
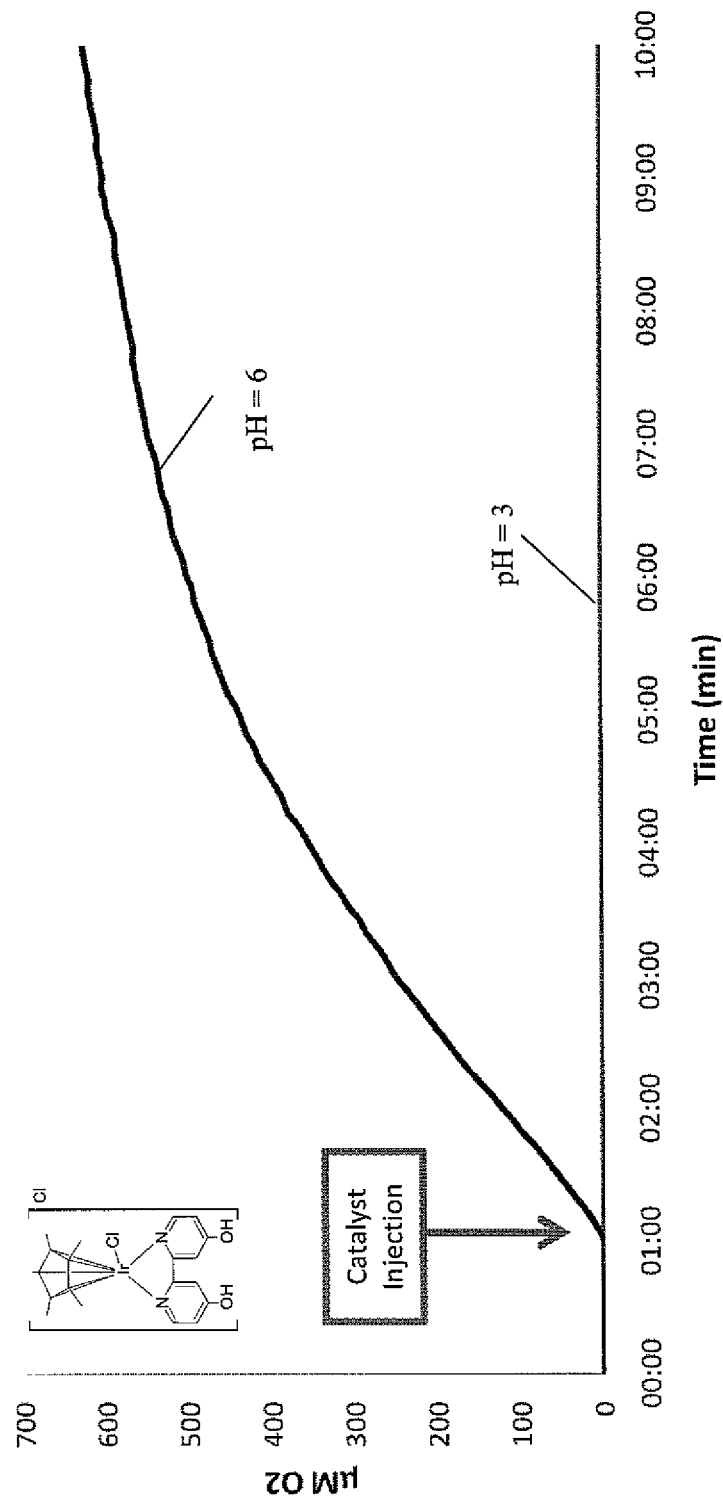
FIG. 3 shows the rate of generation of $O_2$ from water oxidation over time at pH=6 and pH=3.

Catalysts of the formula Cp*IrCl(n,n'-DHBP)]Cl according to the present invention were used for water oxidation at a variety of different pH levels. These catalysts were the same catalysts as the first three catalysts used in Example 6. 5 μM catalyst with 20 mM $NaIO_4$ in 180 mM NaOAc were employed. The results are shown in Table 7 below. The plot of $O_2$ generation over time for Cp*IrCl(4,4'-DHBP)]Cl at pH=3 and pH=6 is shown in FIG. 3.

TABLE 7

Water Oxidation

| Catalyst | 4,4'-DHBP | 6,6'- DHBP | 4,4'-dmeobp |
|---|---|---|---|
| pH = 6 for 10 minutes | | | |
| TON | 124 | 120 | 10 |
| TOF (min$^{-1}$) | 14 | 14 | 1 |

TABLE 7-continued

| | Water Oxidation | | |
|---|---|---|---|
| Catalyst | 4,4'-DHBP | 6,6'-DHBP | 4,4'-dmeobp |
| pH = 3 for 10 minutes | | | |
| TON | 0 | 1.3 | 1.2 |
| TOF (min$^{-1}$) | 0 | 0.14 | 0.12 |
| Enhancement as pH change from 3 to 6 | >124X | 92X | 8X |

Example 8

Figure 4:
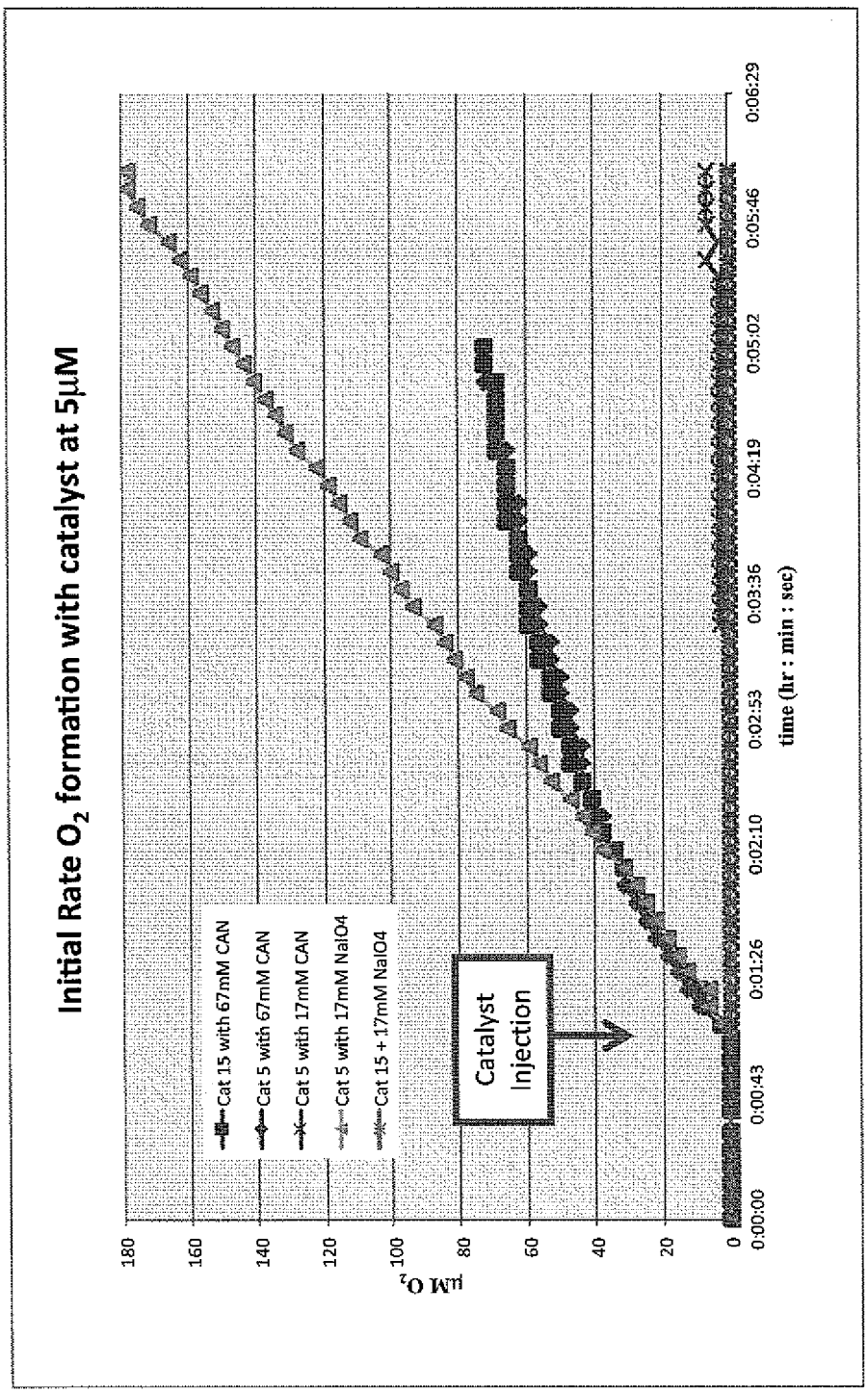
FIG. 4 shows the rate of generation of $O_2$ from water oxidation over time with different oxidants and catalysts as described in example 8.

A catalyst according to the present invention [Cp*Ir$^{III}$(DHBP)Cl]Cl was used for water oxidation with cerium (IV) ammonium nitrate (CAN) as the oxidant. The reaction progress was monitored by a Clark electrode to measure the increase in dissolved oxygen with time in a sealed vessel. For longer reaction times, the amount of oxygen that builds up in the headspace is significant and was measured by pressure transducers. In the first set of experiments, the concentration of catalyst was 5 μM and CAN=67 mM at pH=6.0. The initial rate of oxygen evolution by the catalyst [Cp*Ir$^{III}$(DHBP)Cl]Cl (FIG. 4, "Cat 5+67 mM CAN" denotes) was 31 μM min$^{-1}$ (TOF=6.4 min$^{-1}$, TON=14 in 5 min) No oxygen evolution was observed without CAN or the catalyst. A prior art catalyst, catalyst 15(Cat 15 in FIG. 4, "Cat 15+67 mM CAN") was used as a comparison. The prior art Cat 15 is represented by the formula taken from Blakemore, et al., "Half-sandwich iridium complexes for homogeneous water-oxidation catalysis," *J. Am. Chem. Soc.*, 2010, vol. 132, pp. 16017-16029:

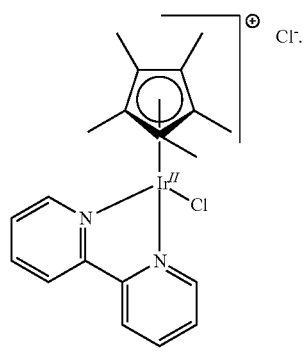

In a second set of experiments, the concentration of catalyst was 5 μM. Cat5 was used in a buffered aqueous solution at pH 5.6 with 17 mM sodium periodate as the oxidant, as shown in green in FIG. 4. The initial rate of oxygen generation was 31 μM min$^{-1}$, TOF=6.3 min$^{-1}$ and TON=36 in 5 min. Significantly, the rate of O$_2$ generation did not level off with time. At higher NaIO$_4$ concentrations, TON=84 in 5 mM, TOF=18 min$^{-1}$. For comparison, the data ("Cat 15+17 mM CAN" in FIG. 4) shows that Cat15 was not active under these conditions. In addition, the data ("Cat 5+17 mM CAN" in FIG. 4) shows that Cat 5 with CAN=17 mM does not oxidize water appreciably.

Example 9

Figure 5:
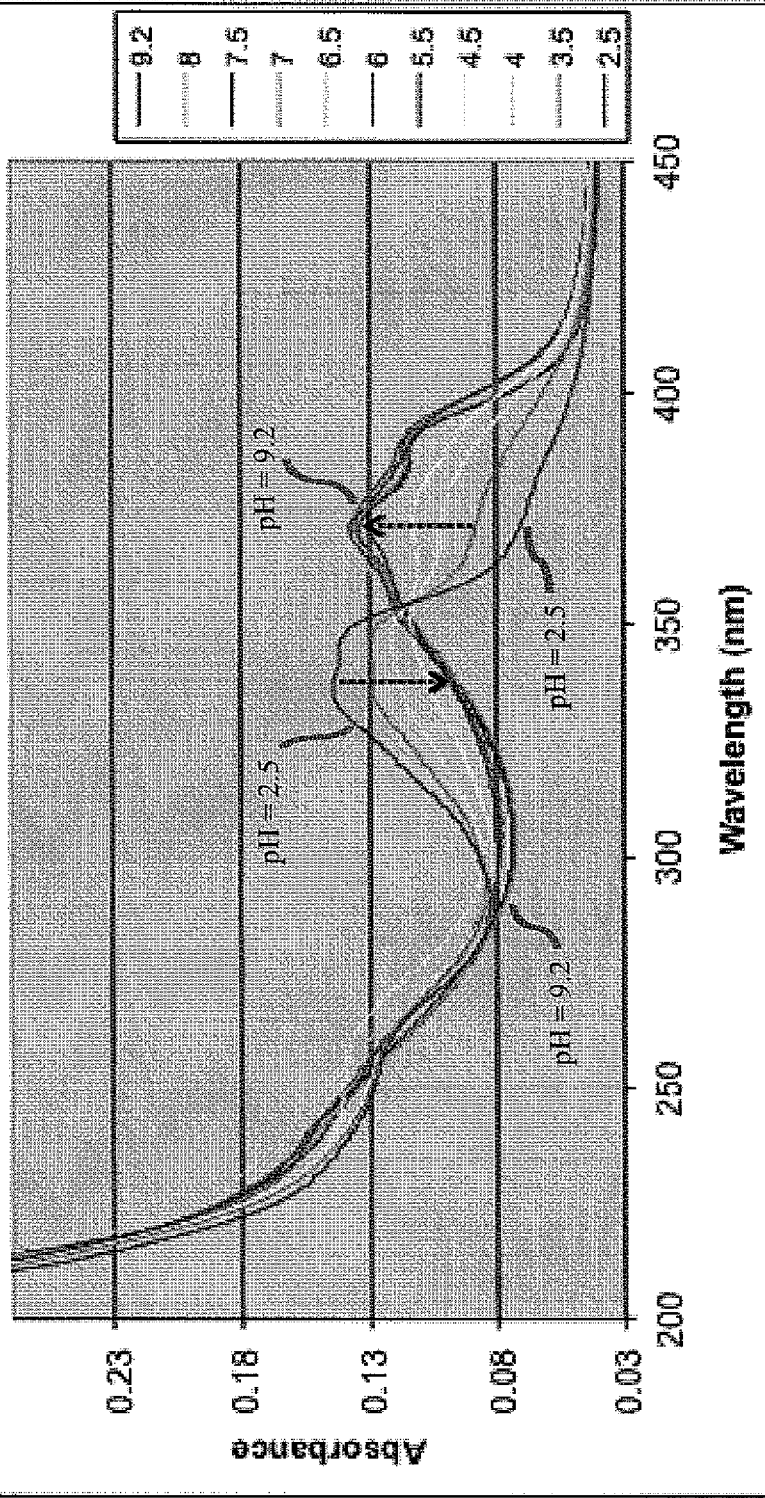
FIG. 5 shows a UV-Vis spectra for [Cp*Ir(6,6'-dhbp)Cl]Cl at various pH levels.

A catalyst according to the present invention [Cp*Ir(6,6'-DHBP)Cl]Cl was studied for its UV-Vis spectra (FIG. 5. Note that the dotted arrows indicate how the spectra change with increasing pH, and the curved lines show the pH values of the plots) at different pH values. Approximately 100 mL of 0.1M Na$_2$HPO$_4$ was put into a beaker and stirred and the pH was recorded. 2 mL of 0.0000034M catalyst was put into 10 mL volumetric flasks (final concentration of Ir complex is 6.8 μM). 100 mL of 0.1M Na$_2$HPO$_4$ was titrated with 0.1M HCl until it reached the desired buffer pH (every 0.5 pH unit). At each desired buffer pH, 8 mL of the solution was put into the volumetric flasks. pH's used were as follows: 9.2, 8.0, 7.5, 7.0, 6.5, 6.0, 5.5, 5.0, 4.5, 4.0, 3.5, 3.0, 2.5. One volumetric flask with [Cp*Ir(6,6'-DHBP)Cl]Cl was prepared for each buffer solution. UV/Vis spectra for each solution were obtained (FIG. 5).

From this example, the pKa value for this catalyst was estimated to be 4.6±0.1 from multiple experiments. This pKa value represents simultaneous removal of both protons from the ligand. It was concluded that the pH sensitive spectroscopic features were due to ligand deprotonation events rather than Ir—OH$_2$ (formed from Ir—Cl) deprotonation.

Figure 6:
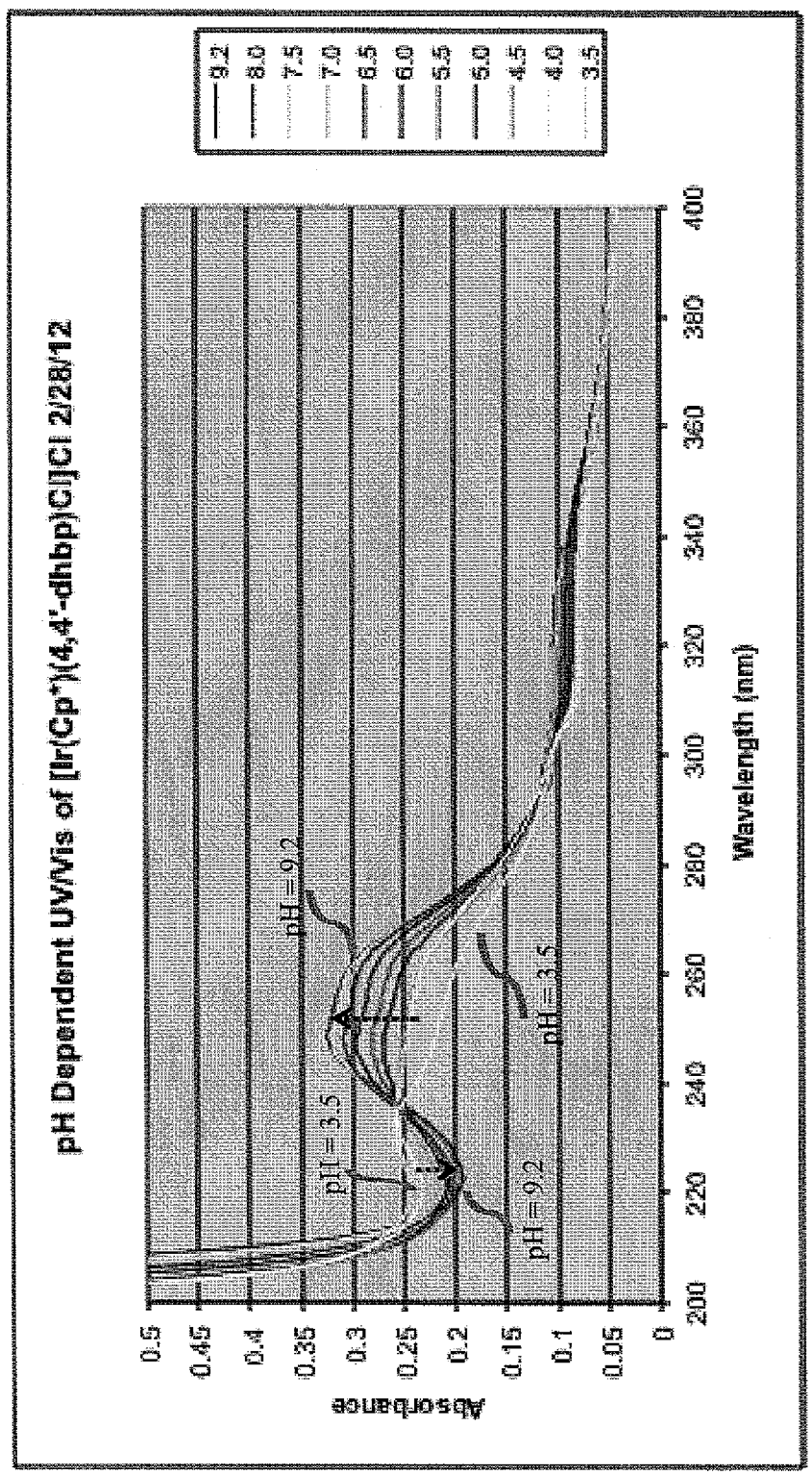
FIG. 6 shows a UV-Vis spectra for [Cp*Ir(4,4'-dhbp)Cl]Cl at various pH levels.

Another catalyst according to the present invention, [Cp*Ir(4,4'-dhbp)Cl]Cl, was subjected to the same procedure. Its UV-Vis spectra are shown in FIG. 6 (note that the dotted arrows indicate how the spectra change with increasing pH, and the curved lines show the pH values of the plots). This experiment indicates a pKa value of 4.4±0.2 from multiple experiments. Again, this pKa value represents simultaneous removal of both protons from the ligand.

Example 10

Figure 7:
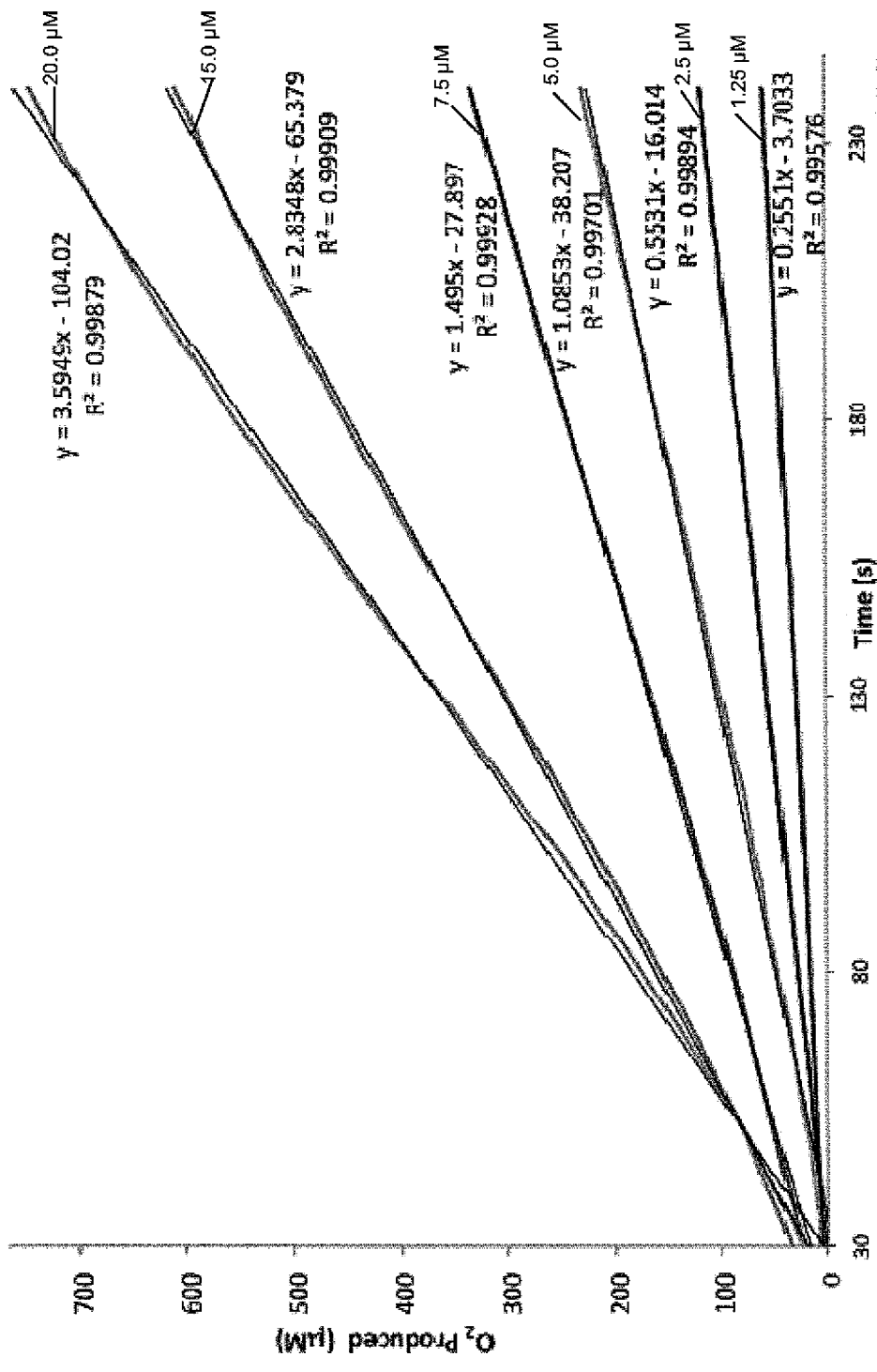
FIG. 7 shows the rate of water oxidation plotted as a function of concentration of the catalyst [Cp*Ir(6,6'-dhbp)Cl]Cl with 17 mM $NaIO_4$ as the oxidant at 25° C.

A catalyst according to the present invention [Cp*Ir(6,6'-DHBP)Cl]Cl was studied to explore the mechanism of catalyzing water oxidation. FIG. 7 shows the amount of oxygen production over time. It was observed that the rate of water oxidation was dependent on the concentration of the catalyst. Rates were most linear from 30 to 240 seconds. The rate law was clearly first order in the catalyst, with a plot of rate vs. concentration giving a clearly linear trend with R$^2$=0.997. Furthermore, a plot of ln(rate) vs. ln([catalyst]) was also linear with slope=0.94. In this analysis, the slope corresponds to reaction order in Ir catalyst. Thus, it seems likely that the catalyst catalyzes water oxidation as a monomeric species.

It was observed that the concentration of oxidant did not appear to have a big impact on the reaction rate, as long as oxidant concentration was at least 10 mM.

The data above suggests that with periodate as the oxidant, the catalyst is a homogeneous molecular catalyst.

Example 11

A catalyst according to the present invention, [Cp*Ir(6,6'-DHBP)Cl]Cl was prepared in a glove box. In a 100 ml Schlenk flask, 6,6'-DHBP (100 mg, 531 μmole), [Cp*IrCl$_2$]$_2$ (211 mg, 266 μmole), and 10 ml of dry DMF were combined. The reaction mixture was a yellow/orange slurry; the flask was sealed, removed from the glove box and placed under nitrogen. The reaction was then heated to 60° C. for 1 day. A bright yellow solution resulted and DMF was removed by vacuum distillation. The residue remaining was dissolved in a minimal amount of methanol then copious amounts of Et$_2$O were added to precipitate out the product. The precipitate was isolated by filtration, washed with more Et$_2$O, dried by high vacuum, and this yielded 205 mg of product (65% yield). This catalyst can also be prepared by a similar procedure using methanol as a solvent, to obtain a similar yield.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. An organometallic complex represented by the formula:

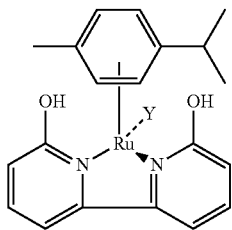

wherein Y is selected from the group consisting of $F^-$, $Cl^-$, $Br^-$, $I^-$, alkoxy groups, $PF_6^-$, $BF_4^-$, $B(ArF)_4^-$, $ClO_4^-$, $SbF_6^-$, $SO_4^{2-}$, trifluoroacetate, and thiocynatates.

2. The organometallic complex of claim 1, wherein Y is selected from the group consisting of $F^-$, $Cl^-$, $Br^-$ and $I^-$.

3. A method for the production of an organometallic complex represented by the formula:

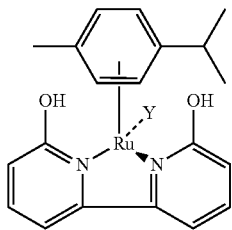

wherein Y is selected from the group consisting of $F^-$, $Cl^-$, $Br^-$, $I^-$, alkoxy groups, $PF_6^-$, $BF_4^-$, $B(ArF)_4^-$, $ClO_4^-$, $SbF_6^-$, $SO_4^{2-}$, trifluoroacetate, and thiocyanates;

starting from a bipyridinone represented by formula:

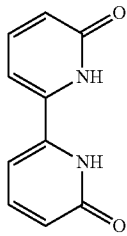

said method comprising the steps of allowing said bipyridinone to tautomerize to produce 6,6'-Dihydroxybipyridine; and reacting said 6,6'-dihydroxybipyridine with a ruthenium metal complex.

4. The method of claim 3, wherein said ruthenium metal complex is $[(p\text{-cymene})RuCl_2]_2$.

5. A method of using an organometallic complex represented by the formula:

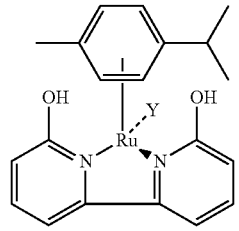

wherein Y is selected from the group consisting of $F^-$, $Cl^-$, $Br^-$, $I^-$, alkoxy groups, $PF_6^-$, $BF_4^-$, $B(ArF)_4^-$, $ClO_4^-$, $SbF_6^-$, $SO_4^{2-}$, trifluoroacetate, and thiocyanates, comprising step of contacting a substrate with a source of hydrogen in the presence of said organometallic complex under conditions suitable to hydrogenate or reduce said substrate.

6. The method of claim 5, wherein said hydrogenation is carried out in an aqueous solution.

7. The method of claim 5, wherein said substrate is $CO_2$, a ketone, or an amine and the reaction is carried out in the presence of a base.

8. A method of using an organometallic complex represented by the formula:

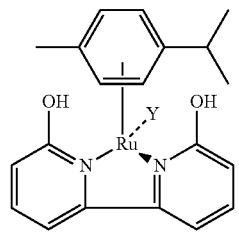

wherein Y is selected from the group consisting of $F^-$, $Cl^-$, $Br^-$, $I^-$, alkoxy groups, $PF_6^-$, $BF_4^-$, $B(ArF)_4^-$, $ClO_4^-$, $SbF_6^-$, $SO_4^{2-}$, trifluoroacetate, and thiocyanates, comprising step of contacting an oxidizing agent with water in the presence of said organometallic complex under conditions suitable for water oxidation.

9. The method of claim 8, wherein said oxidizing agent is selected from the group consisting of an oxidation agent containing metals in a high oxidation state, an oxidizing agent containing non metal in a high oxidation state, sodium periodate, persulfate, cobalt (III) complexes, and ruthenium (III) complexes.

10. The method of claim 8, wherein the water oxidation is driven, at least partially, by sunlight or electricity.

11. The method of claim 8, where said oxidization is carried out in sunlight.

12. A method of using an organometallic complex represented by the formula:

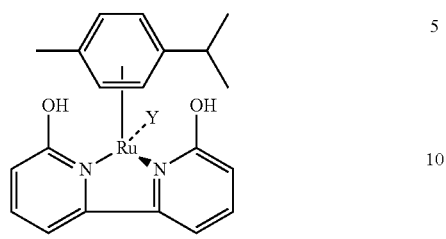

wherein Y is selected from the group consisting of $F^-$, $Cl^-$, $Br^-$, $I^-$, alkoxy groups, $PF_6^-$, $BF_4^-$, $B(ArF)_4^-$, $ClO_4^-$, $SbF_6^-$, $SO_4^{2-}$, trifluoroacetate, and thiocyanates, comprising step of contacting water with an oxidizing agent in the presence of said organometallic complex under conditions suitable to oxidize said water.

* * * * *